(12) United States Patent
Coignet (10) Patent No.: US 7,425,414 B2
(45) Date of Patent: Sep. 16, 2008

(54) METHOD OF PROGNOSIS OF METASTASIS BY DETECTION OF FRA12E FRAGILE SITE WITHIN THE SMRT GENE/LOCUS AT CHROMOSOME 12Q24

(75) Inventor: Lionel J. Coignet, Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 301 days.

(21) Appl. No.: 11/052,344

(22) Filed: Feb. 7, 2005

(65) Prior Publication Data

US 2005/0191674 A1  Sep. 1, 2005

Related U.S. Application Data

(60) Provisional application No. 60/542,538, filed on Feb. 6, 2004.

(51) Int. Cl.
C12Q 1/88 (2006.01)
C07H 21/02 (2006.01)
C07H 21/04 (2006.01)

(52) U.S. Cl. ................. 435/6; 536/23.1; 536/23.5; 536/24.31

(58) Field of Classification Search ............... None
See application file for complete search history.

(56) References Cited

OTHER PUBLICATIONS

NCBI Database, National Center for Biotechnology Information, National Library of Medicine, NIH (Bethesda, MD, USA). GenBank Accession No. AC048340, Apr. 3, 2003.
NCBI Database, National Center for Biotechnology Information, National Library of Medicine, NIH (Bethesda, MD, USA). GenBank Accession No. AC027706, May 2, 2000.
NCBI Database, National Center for Biotechnology Information, National Library of Medicine, NIH (Bethesda, MD, USA). GenBank Accession No. AC068837, Jul. 13, 2000.
NCBI Database, National Center for Biotechnology Information, National Library of Medicine, NIH (Bethesda, MD, USA). GenBank Accession No. AC025685, May 6, 2000.
WO 03/106645 A2 (ISIS Pharmaceuticals, Inc.) Dec. 24, 2003, pp. 5-6.
Amarose et al., *A Heritable fragile 12q24.13 segregating in a family with the fragile X chromosome*, Hum Genet, 1987, pp. 4-6.
Mimori, et al., *Cancer-specific chromosome alterations in the constitutive fragile region FRA3B*, Proc. Natl. Acad. Sci. USA, Jun. 1999, Medical Sciences, vol 96, pp. 7456-7461.
Menin, et al., *Anomalous Transcripts and Allelic Deletions of the FHIT Gene in Human Esophageal Cancer*, Cancer Genet Cytogenet, 2000, vol. 119, pp. 56-61.
Voiculescu, et al., *Homozygous condition for a BrdU-requiring fragile site on chromosome 12*, Hum Genet, 1991, pp. 416-417.
Sutherland, *Heritable Fragile Sites on Human Chromosomes I. Factors Affecting Expression in Lymphocyte Culture*, Am J Hum Genet, 1979, vol. 31, pp. 125-135.
Jiang, et al., *Genomic organization and refined mapping of the human nuclear corepressor2(NCOR2)/silencing mediator of retinoid and thyroid hormone receptor (SMRT) gene on chromosome 12q24.3*, Cytogenet Cell Genet, 2001, vol. 92, pp. 217-220.
Alcock, et al.; Analysis of Colorectal Tumor Progression by Microdissection and Comparative Genomic Hybridization; Genes, Chromosomes & Cancer, vol. 37, No. 4, Aug. 2003; XP-002453927; pp. 369-380.
Bova, et al.; Physical Mapping of Chromosome 8p22 Markers and Their Homozygous Deletion in a Metastatic Prostate Cancer; Genomics, vol. 35, No. 1, 1996; XP-002453929; pp. 46-54.
Coignet, et al.; Alteration of SMRT Tumor Suppressor Function in Transformed Non-Hodgkin Lymphomas; Blood, vol. 98, No. 11 Part 1, Nov. 16, 2001; XP-000808550; p. 760a and 43rd Annual Meeting of the American Society of Hematology, Part 1; Orlando, FL; Dec. 7-11, 2001; ISSN: 0006-4971.
Dohna, et al.; Adrenocortical Carcinoma Is Characterized by a High Frequency of Chromosomal Gains and High-Level Amplifications; Genes, Chromosomes & Cancer, vol. 28, No. 2, Jun. 2000; XP-002453928; pp. 145-152.
Muzny, et al.; *Homo sapiens* 12 BAC RP11-408I18 (Roswell Park Cancer Institute Human BAC Library) complete sequence; Mar. 27, 2003; XP-002453967; 64 pages.
Muzny, et al.; *Homo sapiens* 12 BAC RP11-30G17 (Roswell Park Cancer Institute Human BAC Library) complete sequence; Mar. 27, 2003; XP-002453968; 6 pages.

*Primary Examiner*—Carla Myers
(74) *Attorney, Agent, or Firm*—Hodgson Russ LLP (57) ABSTRACT

Provided are methods for prognostic prediction of metastasis. The method comprises identifying the presence or absence of a fragile site FRA12E on chromosome 12q24 at the SMRT gene locus. The presence of FRA12E in an individual can be determined in cell samples obtained from the individual by hybridization techniques such as fluorescence in situ hybridization techniques. The presence of this fragile site at this locus is indicative of higher likelihood of metastasis than if the fragile site is absent. Also provided are kits for the determination of likelihood of metastasis.

7 Claims, 6 Drawing Sheets

RPCI11 BAC clones

METHOD OF PROGNOSIS OF METASTASIS BY DETECTION OF FRA12E FRAGILE SITE WITHIN THE SMRT GENE/LOCUS AT CHROMOSOME 12Q24

This application claims priority to U.S. provisional application No. 60/542,538 filed on Feb. 6, 2004, the disclosure of which is incorporated herein by reference.

FIELD OF THE INVENTION

This invention relates generally to the field of cancer and more particularly to tools and methods for prognosis of metastatic disease.

DESCRIPTION OF RELATED ART

Metastasis is the spread of cancer from a primary site and the formation of new tumors in distant organs. When cancer is detected at an early stage, before it has spread, it can often be treated successfully by surgery or local irradiation. However, when cancer is detected after it has metastasized, treatments are much less successful. Furthermore, for many patients in whom there is no evidence of metastasis at the time of their initial diagnosis, metastases can occur at a later time, even decades after apparently successful primary treatment.

Metastases can show an organ-specific pattern of spread that might occur years or even decades after apparently successful primary treatment. Breast cancer (BC), the most frequent cancer in the female population of industrialized countries, often metastasizes to bone. Metastases to bone occur in >70% of patients with advance disease. Despite some advances in chemotherapeutic regimens, it is virtually impossible to cure breast cancer-induced metastasis and osteolysis. Metastasis of some other cancers is also considered to be organ specific. For example, prostate cancer is known to spread to bone.

A persistent clinical challenge that spans all types of cancer has been to predict, among a group of individuals having the same types of cancer with similar demographic and disease characteristics, which patients will actually progress from localized to metastatic disease and which will remain disease-free following initial therapy. Despite the clinical importance of metastasis, much remains to be learned about the biology of the metastatic process as well as prediction and predisposition markers. In part, knowledge is limited because metastasis is a 'hidden' process and diagnosis is typically made after metastasis has already occurred. Many molecular factors have been identified as contributing to the formation of detectable metastases. However, the identification of molecules and genes that are associated with a metastatic end point does not, in itself, provide information about how these molecules contribute to the metastatic process and how the process is driven. This knowledge will be important for providing the biological context in which to apply the rapidly increasing information about molecular contributors to metastasis.

To develop metastatic lesions, tumor cells must be able to accomplish each step in the multistep process while avoiding host immune surveillance (1). A series of cellular events appears associated with all metastatic processes. These include interactions of the cancer cells with the surrounding stromal cells; interactions with the extracellular matrix leading to matrix recognition, cell-attachment, release of bioactive matrix-bound factors and matrix destruction for tumor expansion; formation of tumor vasculature or angiogenesis; and escape from immunoprotection and from cell death (2).

A similar pattern of events takes place in the transformation of non-Hodgkin's lymphomas (NHLs) where the development of the full neoplastic phenotype most likely depends on the acquisition of multiple genetic events, including the concurrent activation of synergistic dominant oncogenes and loss of tumor suppressor gene functions (3,4).

While the mechanism of malignancy or metastasis are not completely understood, genetic breakage is one mechanism by which functional loss of tumor suppressor gene activity may occur. Chromosomal locations in which genetic breakage may be induced are known as fragile sites. Fragile sites have been shown to be involved in some malignancies in which the fragile site lies within known genes, such as the FHIT gene (chromosome 3p) in lung cancer, and where small deletions are consistently observed on chromosome 3 (17, 18). These fragile sites are inherited in a dominant Mendelian fashion. They are also known to contain specific motifs repeated more than 200 times. It has previously been shown that two fragile sites exist on the long arm of chromosome 12. FRA12B is located at 12q24.13 (19) and FRA12E has been located at 12q24.2-3 (20). It has been previously estimated that approximately 5% of the human population is positive for one of these two fragile sites. However, the relationship of the fragile sites with metastasis is not clear and accordingly, there is an ongoing need to identify and develop novel markers for metastases.

SUMMARY OF THE INVENTION

The present invention provides a method for the prognostic prediction of metastasis. The method comprises identifying the presence or absence of fragile site FRA12E on chromosome 12q24 at the SMRT gene locus. The presence of this fragile site at this locus is indicative of higher likelihood of metastasis than if the fragile site is absent. The presence of this fragile site may be detected by using as probes nucleotide sequences which can hybridize to the 12q24 locus. Examples of nucleotide sequences that can be used as probes include BAC clones (such as SMRT-specific RPC11 BAC clones).

In one embodiment, the method for detecting the presence of FRA12E site on chromosome 12 in the 12q24 locus comprises the steps of contacting a genomic DNA sample from an individual with one or more labeled BAC clones which comprise sequences corresponding to the 12q24 region at the SMRT gene locus and determining specific binding of the probes. In a preferred embodiment, the specific binding of the probes is determined by fluorescent in situ hybridization (FISH).

In another aspect of the invention, since the fragile site FRA12E is located within or in close proximity to the SMRT gene, a prognostic evaluation predictive of metastasis can also be carried out by determining the expression of the SMRT protein by immunodetection such as by ELISA, Western blotting, fluorescence labeling and the like.

BRIEF DESCRIPTION OF THE DRAWINGS

FIGS. 2C and 2D are representations of immunostaining with anti-SMRT antibody for benign prostate tumor (2C) showing positive staining and metastatic tumor (2D) showing a lack of staining.

FIG. 4. Mapping of the FRA12E fragile site within the SMRT gene. Chromosomes were harvested after induction of the fragile sites with aphidicolin and hybridized with the SMRT-specific RPCI11 BAC clones (FIG. 3) (green) and control BAC clone (red). One chromosome 12 shows a normal pattern of hybridization wherein the predominant signal is yellow (due to the overlapping/juxtaposition of the green and the red signals). The other signal (indicated by short arrow) shows a split green signal, next to a main yellow signal indicating that the BAC clones span a DNA double strand break due to activation of the fragile site. The SMRT specific probe hybridized on both sites of the breakage, giving rise to the split FISH signal. The color of the dots is indicated in the figure.

DETAILED DESCRIPTION OF THE INVENTION

The present invention provides a method for prognosis of metastasis. The present method is based on the findings that the fragile site FRA12E is located on the human chromosome 12a24 at the SMRT gene locus. Further, our results in breast cancer and prostate cancer and the involvement of SMRT down-regulation in several other cancers indicate that this specific fragile site localized within the SMRT locus is directly related to a greater risk of damage to the integrity of SMRT, and can ultimately lead to tumor transformation/metastasis.

SMRT was originally described in 1995 (5) as a protein whose association with nuclear receptors both in solution and bound to DNA response elements is destabilized by ligand. Studies by several groups (6-10) demonstrated that SMRT and a related co-repressor N-CoR (nuclear receptor co-repressor) recruit a transcriptional repression complex, which contains sin3A/B protein and histone deacetylases (HDAC1/2)(11-14) to nuclear receptors. The ability of the "silencing complex" to deacetylate histones results in a condensed chromatin state which can inhibit transcription (15,16). The sequence of the SMRT gene is presented as SEQ ID NO:1.

The method of the present invention makes use of the above observations to provide a method for prognostic determination of metastasis. The term FRA12E as used herein is defined as a break in the genomic sequence of the 12q24 region at the SMRT gene locus. Accordingly, the method comprises the steps of determining a break in the genomic sequence of the SMRT gene locus.

In one aspect of the invention is provided a method for detecting the presence of FRA12E site on chromosome 12 in the 12q24 locus comprising the steps of contacting a genomic DNA sample from an individual with one or more probes. The probes are polynucleotides or oligonucleotides which comprise sequences complementary to the 12q24 region at the SMRT gene locus; and determining specific binding of the probes.

The sequence of the oligonucleotide for hybridization or PCR amplification will depend upon several factors known in the art. Primarily the sequence of the oligonucleotide will be determined by its capacity to bind to the FRA12E site. This determination is well within the purview of those skilled in the art.

Polynucleotides (referred to as "probes" herein) that specifically hybridize to the FRA12E site can be provided alone, in phages, plasmids, phagemids, cosmids, yeast artificial chromosomes (YACs), bacterial artificial chromosomes (BACs) or any other suitable vector without limitation. It is well known in the art that probes for nucleic acid hybridization based detections of complimentary sequences can be as small as 20 bases. Thus, for example when using BAC clones as probes, either the entire BAC clone can be used or portions thereof (20 bases or more) such that detection of the fragile site can be effected. For FISH assays an example of a convenient length of probes which are made up of portions of BAC clones is about 1 kilo base.

In one embodiment, the probes are used in Southern hybridization assays to detect the presence of the FRA12E site. The hybridizations can be carried out on a test sample and compared to a Southern hybridization by standard methods performed on a control sample. Such reactions can be carried out using a single probe or a panel of overlapping probes that span the 12q24 region. Control probes which can hybridize to a region of chromosome 12 outside of the 12q24 region may also be used.

In another embodiment, in situ hybridization techniques can be used. Since a fragile site is a genetic trait, it is present in all cells, therefore, any tissue can be used. For in situ hybridization techniques, typically, cells are harvested from a biological sample using standard techniques. For example, cells can be harvested by centrifuging a biological sample such as blood, and resuspending the pelleted cells. Typically, the cells are resuspended in phosphate-buffered saline (PBS). Alternatively, the cells obtained from blood can be set in culture for a few days (such as 3 days) with phytohemeagglutinin (PHA) to stimulate proliferation of lymphocytes. Prior to harvesting, the cells (such as 24 hours), treatment with a DNA polymerase inhibitor (such as aphidicolin) can be carried out which facilitates visualization of fragile sites.

After harvesting, the cells can be fixed, for example, in acid alcohol solutions, acid acetone solutions, or aldehydes such as formaldehyde, paraformaldehyde, and glutaraldehyde. To obtain chromosome preparations, cells are cultured for 1 to 3 days. A blocker (such as Colcemid) is added to the cultures to block the cells in metaphase, where chromosomes are highly condensed and can be visualized. Chromosome preparations are then fixed (such as with a solution of methanol/acetic acid (3:1 vol/vol) and then spread onto slides. Pretreatments (such as RNase and pepsin) can be applied to the preparations to potentially lower the background and to facilitate the penetration of the probes in the nuclei, respectively.

The cell suspension is applied to slides such that the cells are preferably present as a single layer. Cell density can be measured by a light or phase contrast microscope. Prior to in situ hybridization, chromosomal probes and chromosomal DNA are denatured. Denaturation typically is performed by incubating in the presence of high pH, heat (e.g., temperatures from about 70° C. to about 95° C.), organic solvents such as formamide and tetraalkylammonium halides, or combinations thereof For example, chromosomal DNA can be denatured by a combination of temperatures above 70° C. (e.g., about 73° C.) and a denaturation buffer containing 70% formamide and 2×SSC (0.3M sodium chloride and 0.03 M sodium citrate); Denaturation conditions typically are established such that cell morphology is preserved. Chromosomal probes can be denatured by heat. For example, probes can be heated to about 73° C. for about five minutes.

After denaturation, hybridization is carried out. Hybridization conditions vary, depending on the concentrations, base compositions, complexities, and lengths of the probes, as well as salt concentrations, temperatures, and length of incubation. The higher the concentration of probe, the higher the probability of forming a hybrid. For example, in situ hybridizations are typically performed in hybridization buffer containing 1-2×SSC, 50% formamide and blocking DNA to suppress non-specific hybridization. In general, hybridization conditions, as described above, include temperatures of about 25° C. to about 55° C., and incubation lengths of about 0.5 hours to about 96 hours. More particularly, hybridization can be performed at about 32° C. to about 40° C. for about 2 to about 16 hours.

Non-specific binding of chromosomal probes to DNA outside of the FRA12E region can be reduced by a series of washes. Temperature and concentration of salt in each wash depend on the desired stringency. For example, for high stringency conditions, washes can be carried out at about 65° C. to about 80° C., using 0.2× to about 2×SSC, and about 0.1% to about 1% of a nonionic detergent such as Nonidet P-40 (NP40). Stringency can be lowered by decreasing the temperature of the washes or by increasing the concentration of salt in the washes.

Chromosomal probes typically are chosen for maximal sensitivity and specificity. The probes generally range from about 50 to about $1 \times 10^5$ nucleotides in length. Chromosomal probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. Fluorophores of different colors are chosen such that each chromosomal probe in the set can be distinctly visualized. Suitable fluorophores include: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5- (and -6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade,™ blue acetylazide (Molecular Probes, Inc., Eugene, Oreg.). Probes are viewed with a fluorescence microscope and an appropriate filter for each fluorophore. Alternatively, techniques such as flow cytometry can be used to examine the hybridization pattern of the chromosomal probes.

Probes also can be indirectly labeled with biotin or digoxygenin, or labeled with radioactive isotopes such as $^{32}$P and $^{3}$H, although secondary detection molecules or further processing then is required to visualize the probes. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Examples of test probes useful for detecting the presence of FRA12E include portions of, or the entire SMRT gene locus. These sequences can be present as part of BAC clones (such as clones from the RPCI BAC library). The sequences of these clones are easily accessed through GenBank at the National Center for Biotechnology Information (NCBI). Examples include polynucleotides comprising sequences corresponding to genomic BAC constructs BAC-RP11-339B19, BAC-RP11-665C13, BAC-RP11-677L6, BAC-RP11-408I18 and BAC-RP11-30G17 (RPCI BAC library). While any one of these probes (or sequences corresponding to a portion of, or the entire probe) can be used, it is preferable to use more than one probe such that the entire sequence of the SMRT gene locus is covered. For example, by using a panel of probes such as BAC-RP11-339B19, BAC-RP11-665C13 and BAC-RP11-677L6, a break in the sequence of the entire SMRT gene locus can be assessed. Therefore, these nucleotide sequences can be used to detect the presence of the FRA12E fragile site as a marker for the progression of cancer to metastatic disease/transformation and as a predictor factor for cancer patients to develop metastatic disease. Negative control probes comprising nucleotide sequences corresponding to regions of chromosome 12 outside the 12q24 region, such as BAC RP11-469A24 (RPCI BAC library), can be used to increase the accuracy of results.

The prognostic test can be used to screen individuals diagnosed with malignancies to predict a likelihood of metastasis. This test can also be used in the general population as an identifier of individuals as being carriers of this fragile site. The FISH test itself is a simple test and can be performed in any diagnostic conventional cytogenetic laboratory.

In another aspect, kits for performing the prognostic tests provided by the invention are provided. The kits comprise test probes and optionally negative control probes. For example, the kit comprises probes comprising sequences corresponding to BAC clones which hybridize to the 12q24 region of chromosome 12 at the SMRT gene locus. In one embodiment, the test probes are polynucleotides corresponding to sequences of BAC-RP11-339B19, BAC-RP11-665C13, and BAC-RP11-677L6. The test probes have fluorescent labels thereon (such as fluorescein or rhodamine and the like). The negative control probes have a fluorescent label which is different from the label on the test probes. Optionally, the kits can also include a DNA polymerase inhibitor (such as aphidicolin)—either in a solution form or as a powder, which facilitates the visualization of fragile sites. Further, cell lines that have been tested and identified to be either positive or negative for the fragile site can also be included in the kits.

The invention is further described by the examples presented below. These examples are illustrative and not intended to be restrictive in any way.

EXAMPLE 1

Figure 1A:
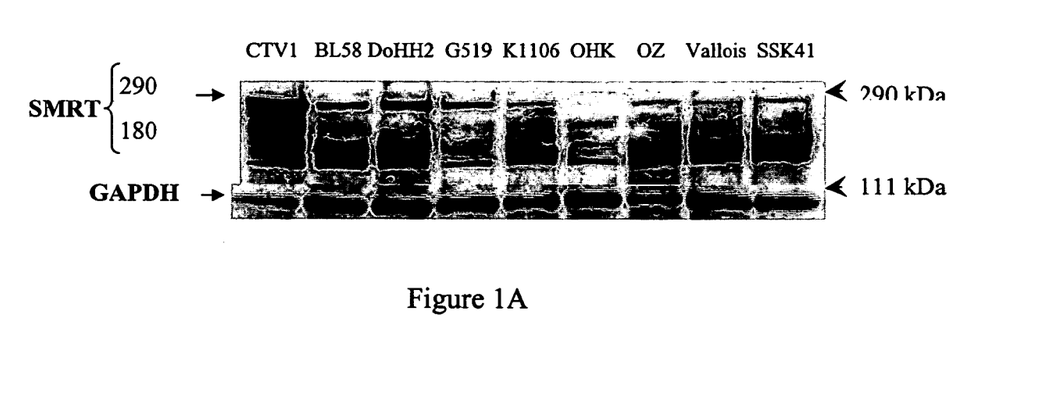
FIGS. 1A and 1B: Western blot analysis of different malignant cell lines with an anti-SMRT antibody. 1A: CTV1=AML cell line (control), all the other lines are transformed NHLs. 1B: MCF7: metastatic breast cancer cell line and MCF10A, its non malignant counterpart; Col2: metastatic colorectal cancer; LnCAP: non-metastatic prostate; PC3: metastatic prostate; Hec1a: metastatic endometrial cancer; A549: metastatic non-small cell lung carcinoma; PIG1: immortalized keratinocytes; F002: melanoma in situ; M1123, M14 and G24: metastatic melanoma cell lines.
Figure 1B:
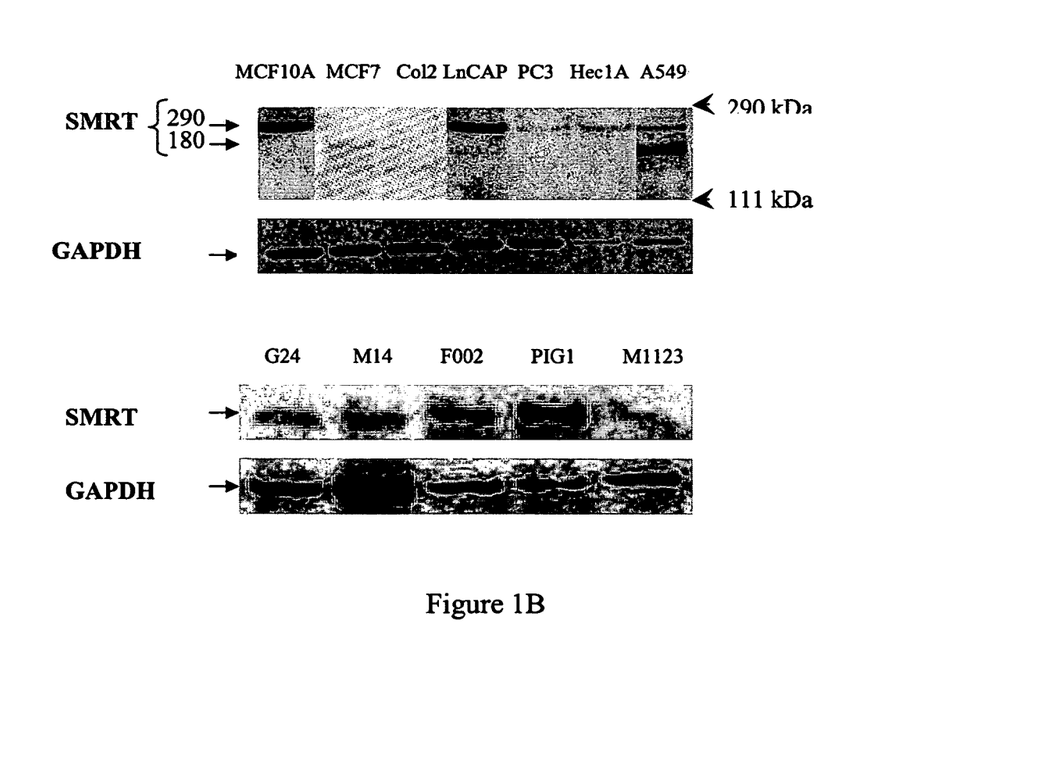

This example demonstrates that the SMRT gene is down-regulated in metastatic cells. To illustrate this, the expression of SMRT gene was determined in several metastatic cell lines. Total protein was extracted from the different cell lines and subjected to Western blotting using a polyclonal anti-SMRT antibody. As shown in FIG. 1, western blot analysis of a series of metastatic cell lines showed a marked SMRT down-regulation of SMRT in most of cell lines examined.

EXAMPLE 2

Figure 2:
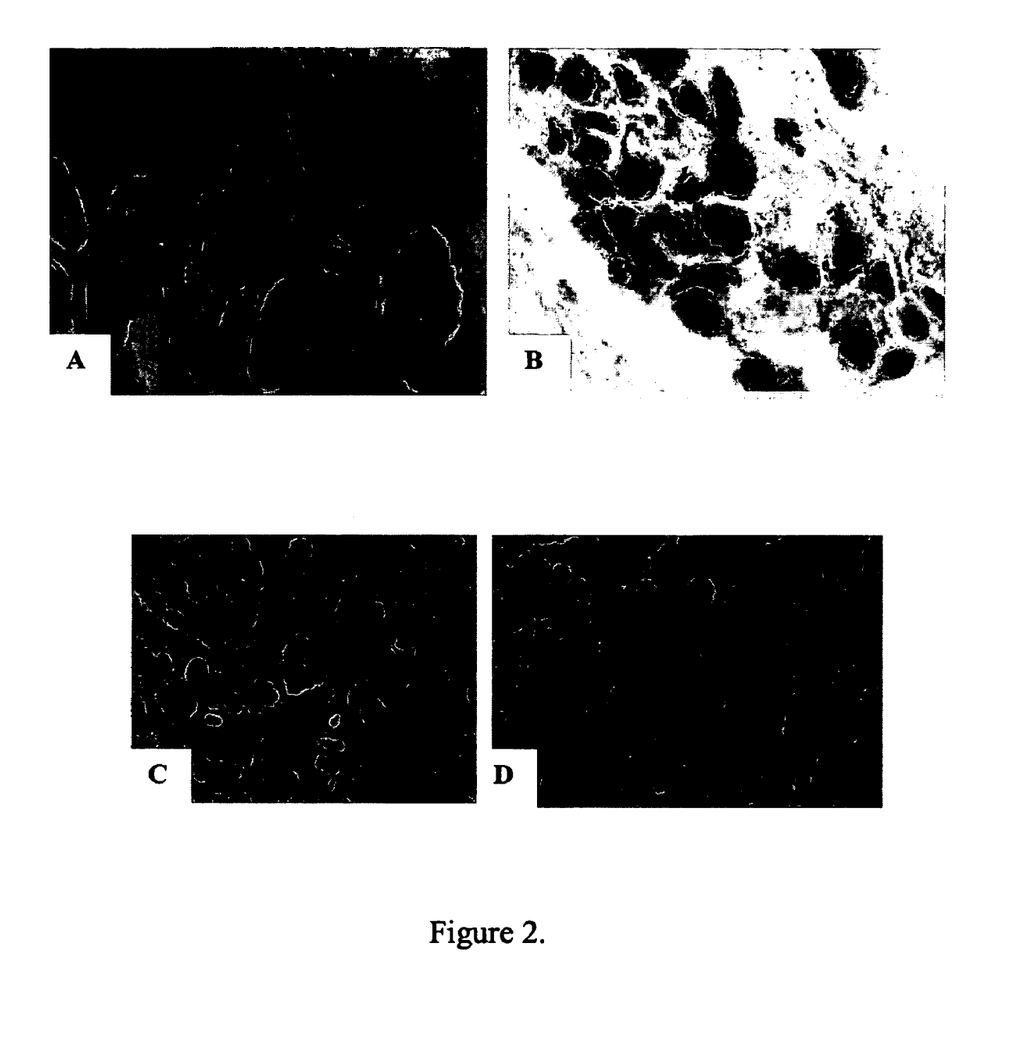
FIG. 2. Immunostaining with an anti-SMRT antibody on breast cancer paired samples 2A) primary tumor and 2B) metastatic tumor, from the same patient. Nine paired samples were studied. Seven out of nine showed the same differential pattern of expression as shown in this figure i.e., positive in the primary tumor and negative in the metastatic tumor. The two other cases showed positive staining for both primary and metastatic tumor. The difference between the two groups of patients (+ or − SMRT in the metastatic tumor) is that average time from primary diagnostic to metastatic disease diagnosis goes from 2 years (for the ± cases) to 9 years (for the +/+ cases).

In this example, the down regulation of the SMRT gene was tested in breast cancer (BC). SMRT gene expression in several breast cancer cell lines was determined as described in Example 1. The results demonstrate that BC cell lines as well as samples from BC patient with metastatic disease have altered SMRT expression (FIG. 1B). Further, 7 out of nine paired breast cancer samples (primary and metastatic tumors from the same patient) presented a positive staining in the primary tumor and negative in the metastatic sample. An example is shown in FIG. 2. Similar results were obtained in prostate tumors wherein 6 out of 8 tumors presented a negative staining in the metastatic sample.

EXAMPLE 3

In this example, immunostaining data was obtained for SMRT from tissue microarrays for samples of breast, prostate, colorectal, lung and ovarian cancer. Each array was made up of 150 to 200 samples. The results are shown in Table 1. Numbers given are percentages of tumors with loss of SMRT expression.

TABLE 1

| Tissue | Benign | Primary | Androgen Dependent | Androgen Independent | Lymph Node Mets | Distant Mets |
|---|---|---|---|---|---|---|
| Prostate | 0 | 10 | 24 | 40 | NA | 67 |
| Breast | NA | 25 | NA | NA | 40 | 77 |
| Colorectal | NA | 10 | NA | NA | 25 | 70 |
| Ovarian | NA | 25 | NA | NA | 40 | 75 |
| Lung | NA | 15 | NA | NA | 25 | 65 |

These data indicate a correlation of the lack of SMRT expression with the stage of the disease, with primary tumors showing less incidence of SMRT negativity.

EXAMPLE 4

The FRA12E region corresponds to the site of SMRT (12q24.2). We tested the hypothesis that inactivation of SMRT in metastatic/transformed tumors is due to a chromosomal breakage at 12q24 due to the presence of this fragile site. Further, if the presence of this fragile site explains the recurrence of breakpoints at 12q24 within SMRT, their presence may represent a predisposition status for these individuals to transformation of NHL or metastasis of solid tumors.

To assess whether the FRA12E fragile site is localized within the SMRT gene, we conducted a study where normal lymphocytes were cultured in the presence of aphidicolin (an inducer of fragile sites) and metaphase chromosomes were subsequently prepared as described below. These preparations were then subjected to fluorescence in situ hybridization using a set of SMRT-specific RPCI BAC clones (FIG. 3A).

Figure 3A:
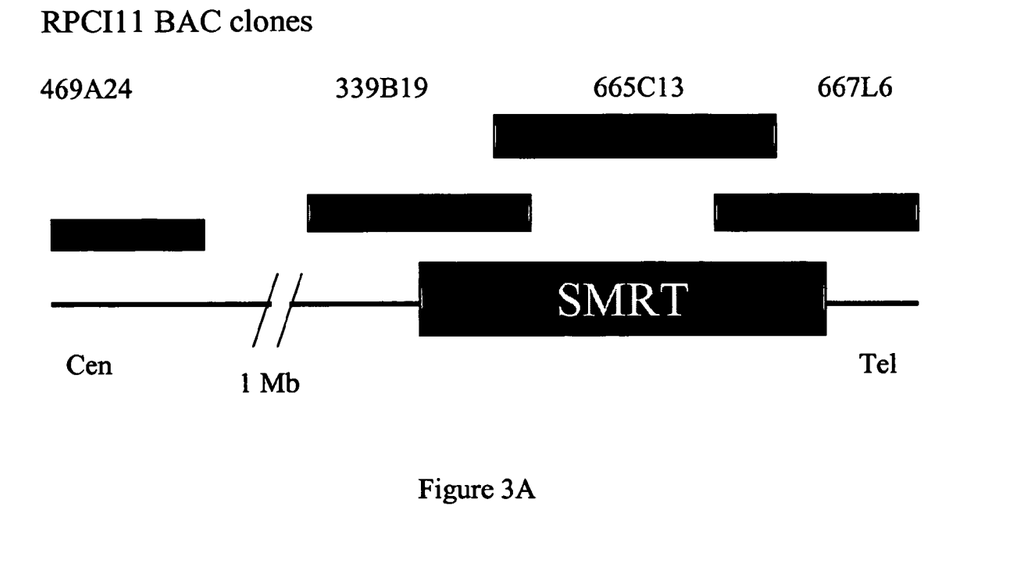
FIGS. 3A and 3B. Schematic representation mapping of the RPCI11 BAC clones used to detect and map the FRA12E fragile site within the SMRT gene. A: BAC clones 339, 665 and 667 are encompassing the SMRT locus; BAC 469 is used as a control probe. B: Schematic representation of the potential spreading of breakages over the SMRT locus, illustrating the need for the use of a set of probes to detect all potential breakages.

Three RPCI11 BAC clones encompassing the SMRT locus were used in our experiments and are depicted as green bars in FIG. 3A. These clones have been sequenced through the Human Genome project. The GenBank references for these sequences are: cen: AC068837 (BAC-RP11-339B19), AC027706 (BAC-RP11-665C13), AC025685 (BAC-RP11-677L6) tel. (NCBI website-www.ncbi.nlm.nih.gov/). Other BAC clones can correspond to these sequences, such as AC073916 (BAC-RP11-408118) and AC069261 (BAC-RP11-30G17). Any polynucleotide sequence or a set of polynucleotides or clones which covers part or all of the SMRT locus can be used. In one embodiment, sequences which cover the entire SMRT gene locus are used. The sequence of this locus has been described in Jiang et al. Clones lacking this sequence such as a BAC clone telomeric to this group of BAC, can be used as a control probe. An example of a control probe is GenBank reference AC048340 (BAC-RP11-469A24).

BAC DNA labeling was done as follows. The BAC DNAs were extracted using a DNA extraction kit (Qiagen). DNA was then subject to nick translation labeling with fluorochrome-conjugated nucleotides using a commercially available kit (Vysis, Downers Grove, Ill.). The SMRT-specific clones were labeled in green whereas the control was labeled in red.

For chromosome preparation, the following procedure was used. One tube of peripheral blood was obtained from cancer patients and controls. The blood was set for a 3-days culture in 10 ml of RPMI medium, supplemented by 10% of fetal calf serum and antibiotics, with 135 µg/ml of PHA. Twenty-four hours before harvesting chromosomes, aphidicolin (0.2 µg/ml) was added to the culture in order to induce fragile sites. Chromosome harvesting was then carried out according to classical cytogenetic techniques for chromosome preparations. Microscope slides were then prepared for hybridization with the labeled BAC clones.

Fluorescence in situ hybridization was carried out as follows. Hybridization was carried out according to established protocols (21). A mixture containing one hundred nanogram of each labeled BAC DNA was applied to the chromosome preparation after denaturation. Hybridization was carried out overnight and slides were washed the next morning. Slides were mounted with antifade solution prior to be observed under a UV microscope with the appropriate filters for the assessment of the signals.

Figure 3B:
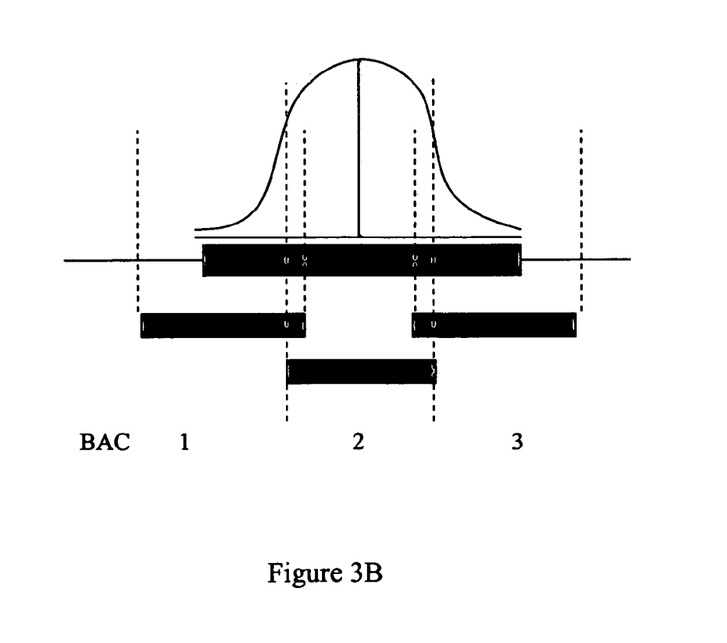
Figure 4:
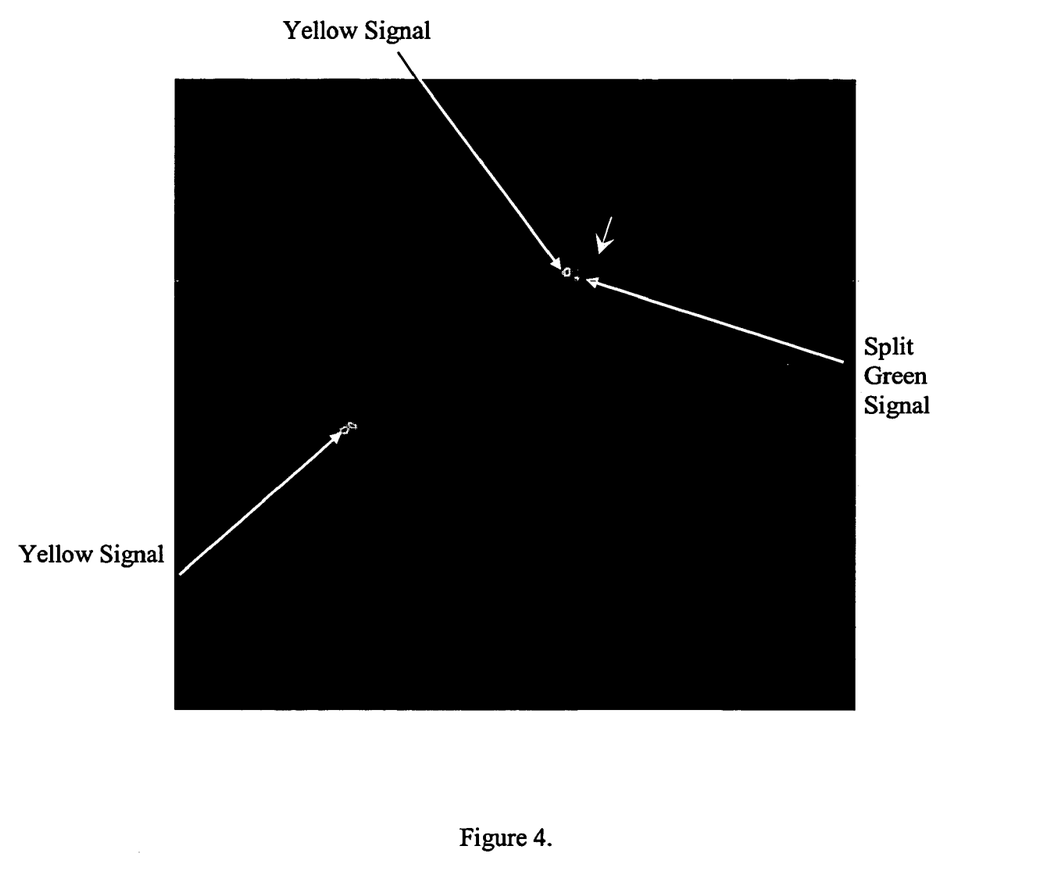

As shown in FIG. 3B, it is necessary to use overlapping clones that encompass the entire SMRT locus in order to detect any and all the breakages in that region. Indeed, the potential breakage in each given chromosome 12 can be scattered over the entire locus, therefore an accurate detection of the fragile site calls for a set of probes covering the entire locus. Using this approach, we were able to demonstrate that the FRA12E fragile site is localized within the SMRT gene (FIG. 4). This figure shows two signals. The upper right hand corner signal (identified by the short arrow) is characterized by a large signal in yellow due to the SMRT-specific green signal mixed with the control probe red signal. In addition, split green signals can be observed just to the right of this first yellow signal. The split greet signals represent the presence of the fragile site. The FISH signal present at the bottom left hand corner shows mostly yellow color signal, due to the overlapping/juxtaposition of the SMRT-specific probes green signals with the red signal from the control probe. No split green signal is observed in this case indicating the absence of the fragile site.

EXAMPLE 5

To test if the SMRT alterations observed in transformation/metastasis might be the consequence of the presence of this fragile site (FRA12E) in its sequence, we conducted a study with breast cancer patients, where we compared the incidence of the fragile site in the blood cells of patients with BC and metastatic disease, patients with BC without metastatic disease and normal population. We recruited three groups of patients, with breast cancer with metastatic disease, with breast cancer without metastatic disease and without breast cancer. Peripheral blood was collected and subject to chromosome preparation, as described above. The results obtained in this study (FIG. 5) show that 100% of BC patients presenting "early" metastatic disease are carriers of the fragile site. As indicated in the figure, two metastatic patients showed to be non-carrier. They correspond to one patient with metastatic disease that developed nine years after their primary diagnostic and one case of untreated cancer as compared with 7% in normal controls. In patients with BC without metastatic disease, two groups are represented, 50% non-carrier and 50% carrier. The patients in the non-metastatic group were within 1-2 years of their primary diagnosis. These cases can be followed clinically to see whether those that are carrier of the FRA12E further develop metastatic tumors. Statistical analysis showed that the variation between the mean from the control group and the metastatic group is significant ($p=0.000441 \times 10^{-3}$). Similarly, the variation between the mean from the carrier versus non-carrier in the non-metastatic group is also significant ($p=0.00168 \times 10^{-6}$). On the other hand, this analysis shows that the variation between the mean from the control group and the non-carrier from the non-metastatic group as well as the variation between the mean from the metastatic group and the carrier group from the non-metastatic group are not significant ($p=0.06$ and $0.748$, respectively).

Figure 5:
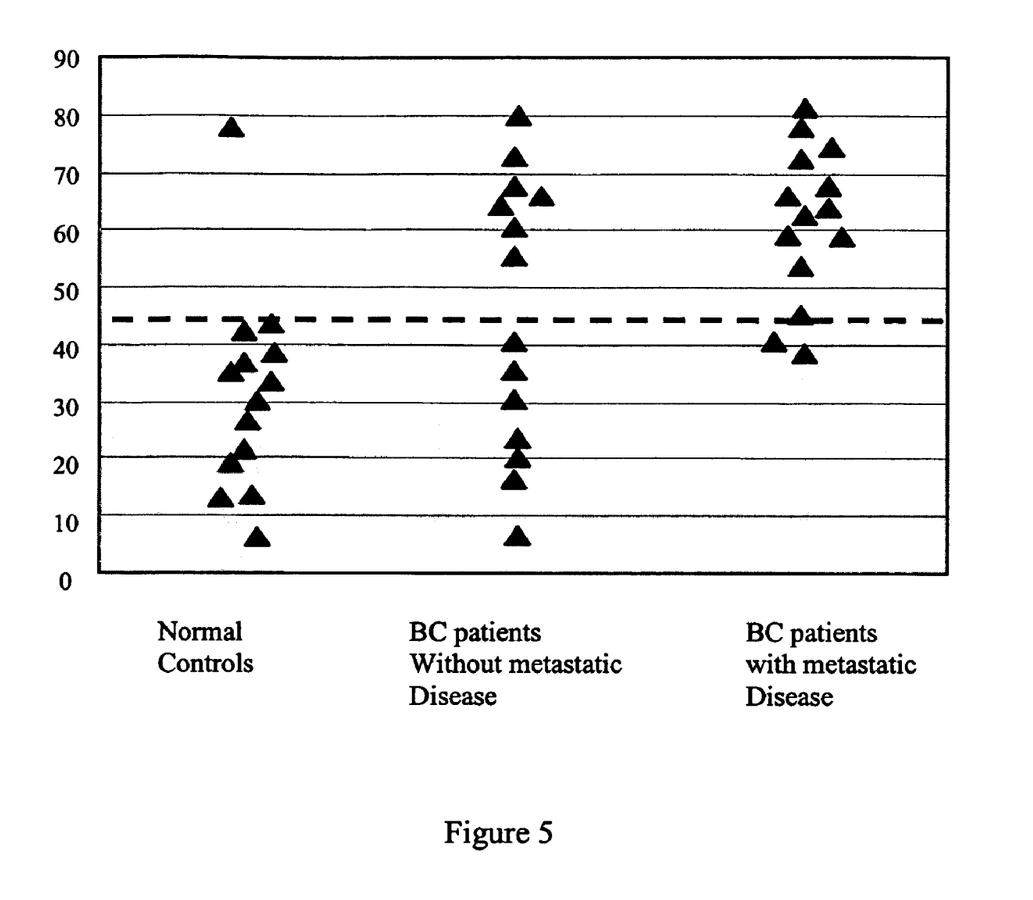
FIG. 5. Schematic representation of the detection of the FRA12E fragile site in peripheral blood samples from normal controls and patients with breast cancer, with or without metastatic disease. This graph provides the percentage of metaphase chromosomes with disrupted FISH signals (indicative of FRA12E breaks) in a patient. Each dot represents a patient sample, the dotted line, the cut off value that allows the best discrimination between the different groups and determining the status of a sample (carrier or not). The two last categories represent additional patient samples tested that have metastatic prostate cancer and melanoma.

As shown in FIG. 5, we tested additionally 4 samples from metastatic prostate cancer (2) and metastatic melanoma (2). Our analysis showed that these patients were also carriers for the FRA12E fragile site. These data demonstrate that the present invention can be used for prediction of prognosis of metastatic disease.

Figure 6:
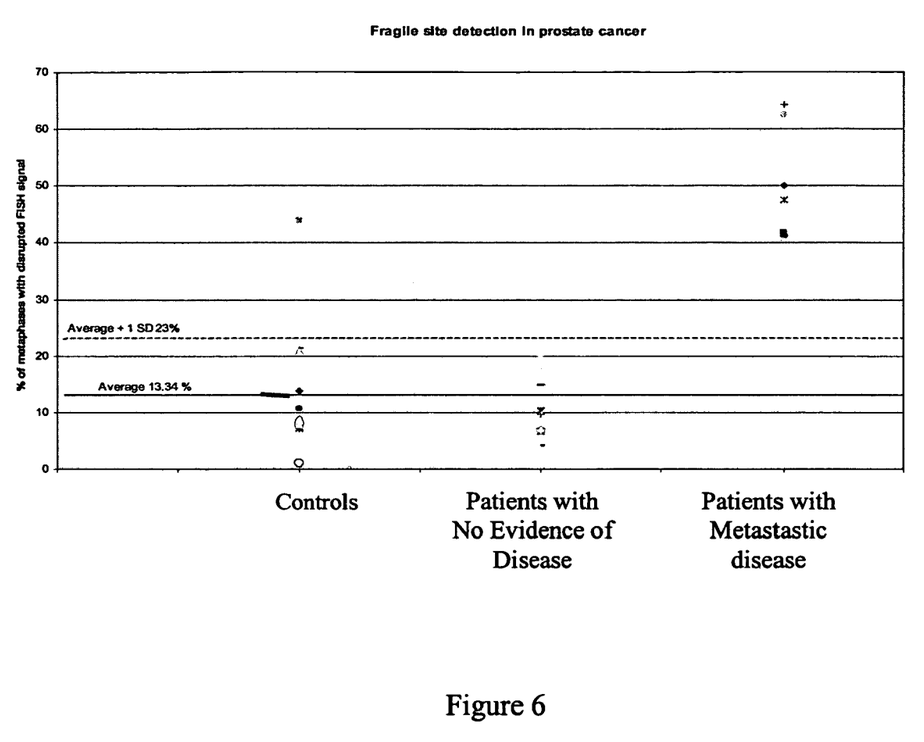
FIG. 6. Schematic representation of the detection of the FRA12E fragile site in peripheral blood samples from normal controls and patients with prostate cancer, with or without metastatic disease. This graph provides the percentage of metaphase chromosomes with disrupted FISH signals (indicative of FRA12E breaks) in a patient. Each dot represents a patient sample, the dotted line, the cut off value that allows the best discrimination between the different groups and determining the status of a sample (carrier or not).

In another illustration of this embodiment, we performed a similar study with protstate cancer patients and controls as shown in FIG. 6. Each group had 14 patients. We similarly found that one control out of 14 was carrier of the fragile site, none of the prostate cancer patients that did not develop metastatic tumors were carrier whereas all of the patients that developed metastatic disease were carriers ($p<0.0001$).

While the present invention has been described using the above examples, routine modifications to this invention will be apparent to those skilled in the art and are intended to be within the scope of the invention.

REFERENCES

1—Yoneda T., Williams P., Hiraga T., Niewolna M., Nishimura R. A bone-seeking clone exhibits different biological properties from the MDA-MB-231 parental breast cancer cells and a brain-seeking clone in vivo and in vitro. J. Bone Miner. Res., 16: 1486-1495, 2001.

2—Fidler I. Modulation of the organ microenvironment for treatment of cancer metastasis. J. Natl. Cancer Inst. (Bethesda), 87: 1588-1592, 1995.

3—Korsmeyer S J (1992). BCL-2 initiates a new category of oncogenes: regulators of cell death. Blood, 80: 879-886.

4—Hahn W C, Counter C M, Lundberg A S, Beijersbergen R L, Brooks M W, Weinberg R A Creation of human tumour cells with defined genetic elements. Nature Jul. 29, 1999; 400(6743):464-8

5—Chen J D, Evans R M A transcriptional co-repressor that interacts with nuclear hormone receptors. Nature Oct. 5, 1995;377(6548):454-7

6—Heinzel T, Lavinsky R M, Mullen T M, Soderstrom M, Laherty C D, Torchia J, Yang W M , Brard G, Ngo S D, Davie J R, Seto E, Eisenman R N, Rose D W, Glass C K, Rosenfeld M G A complex containing N-CoR, mSin3 and histone deacetylase mediates transcriptional repression. Nature May 1, 1997;387(6628):43-8

7—Nagy L, Kao H Y, Chakravarti D, Lin R J, Hassig C A, Ayer D E, Schreiber S L, Evans R M Nuclear receptor repression mediated by a complex containing SMRT, mSin3A, and histone deacetylase. Cell May 2, 1997;89(3): 373-80

8—Alland L, Muhle R, Hou H Jr, Potes J, Chin L, Schreiber-Agus N, DePinho R A Role for N-CoR and histone deacetylase in Sin3-mediated transcriptional repression. Nature May 1, 1997;387(6628):49-55

9—Laherty C D, Yang W M, Sun J M, Davie J R, Seto E, Eisenman R N Histone deacetylases associated with the mSin3 corepressor mediate mad transcriptional repression. Cell May 2, 1997;89(3):349-56

10—Zhang Y, Iratni R, Erdjument-Bromage H, Tempst P, Reinberg D Histone deacetylases and SAP18, a novel polypeptide, are components of a human Sin3 complex. Cell May 2, 1997;89(3):357-64

11—Taunton J, Hassig C A, Schreiber S L A mammalian histone deacetylase related to the yeast transcriptional regulator Rpd3p. Science Apr. 19, 1996;272(5260):408-11

12—Yang W M, Inouye C, Zeng Y, Bearss D, Seto E Transcriptional repression by YY1 is mediated by interaction with a mammalian homolog of the yeast global regulator RPD3. Proc Natl Acad Sci U S A Nov. 12, 1996;93(23): 12845-50

13—Ayer D E, Lawrence Q A, Eisenman R N Mad-Max transcriptional repression is mediated by ternary complex formation with mammalian homologs of yeast repressor Sin3. Cell Mar. 10, 1995;80(5):767-76

14—Schreiber-Agus N, Chin L, Chen K, Torres R, Rao G, Guida P, Skoultchi A I, DePinho R A An amino-terminal domain of Mxi1 mediates anti-Myc oncogenic activity and interacts with a homolog of the yeast transcriptional repressor SIN3. Cell Mar. 10, 1995;80(5):777-86

15—Grunstein M Histone acetylation in chromatin structure and transcription. Nature Sep. 25, 1997;389(6649):349-52

16—Wolffe A P Transcriptional control. Sinful repression. Nature May 1, 1997;387(6628):16-7

17—Mimori K, Druck T, Inoue H, Alder H, Berk L, Mori M, Huebner K, Croce C M Cancer-specific chromosome alterations in the constitutive fragile region FRA3B. Proc Natl Acad Sci U S A Jun. 22, 1999;96(13):7456-61

18—Menin C, Santacatterina M, Zambon A, Montagna M, Parenti A, Ruol A, D'Andrea EAnomalous transcripts and allelic deletions of the FHIT gene in human esophageal cancer. Cancer Genet Cytogenet 2000 May;119(1):56-61
19—Voiculescu I, Back E, Schempp W. Homozygous condition for a BrdU-requiring fragile site on chromosome 12. Hum Genet 1991 February;86(4):416-7.
20—Sutherland G R Heritable fragile sites on human chromosomes: Factor affecting expression in lymphocyte culture. Am J Hum Genet 31: 136-148.
21—Q Jiang, S Galiègue-Zouitina, C Roumier, M P Hildebrand, S Thomas, *LJ Coignet*. Genomic organization and refined mapping of the human silencing mediator of retinoid and thyroid hormone receptor (smrt) on chromosome 12q24.3. Cytogenet Cell Genet, 97: 217-220.

The invention claimed is:

1. A method of determining the likelihood of breast cancer metastasis, melanoma metastasis, or prostate cancer metastasis in a human individual comprising the steps of:
   a) providing a biological sample comprising a chromosomal preparation from the human individual;
   b) performing fluorescent in situ hybridization (FISH) on the chromosomal preparation using the probes bacterial artificial chromosome (BAC) RP11-339B19, BAC RP11-677L6, and BAC RP11-665C13; and
   c) detecting a split FISH signal from said probes as indicative of a break in the sequence of human chromosome 12q24 at the SMRT gene locus,
   wherein the presence of said break is indicative that the individual has an increased likelihood of breast cancer metastasis, melanoma metastasis, or prostate cancer metastasis, should the individual have or develop breast cancer, melanoma, or prostate cancer.

2. The method of claim 1, wherein the sample is a blood sample.

3. The method of claim 1, wherein the individual has been diagnosed with or is at risk for a cancer selected from the group of cancers consisting of breast cancer, melanoma and prostate cancer.

4. The method of claim 3, wherein the cancer is breast cancer.

5. The method of claim 3, wherein the cancer is prostate cancer.

6. The method of claim 1, further comprising using a negative control probe to perform the FISH wherein the negative control probe comprises a chromosome 12 DNA sequence outside the 12q24 region.

7. The method of claim 6, wherein the negative control probe is BAC RP11-469A24.

* * * * *

SEQUENCE LISTING

<160> NUMBER OF SEQ ID NOS: 1

<210> SEQ ID NO 1
<211> LENGTH: 8561
<212> TYPE: DNA
<213> ORGANISM: Homo sapiens
<220> FEATURE:
<223> OTHER INFORMATION: SMRT gene which includes the open reading frame
      for SMRT protein. The open reading frame starts at nucleotide 2
      and ends at nucleotide 7551.

<400> SEQUENCE: 1

```
catgtcgggc tccacacagc ttgtggcaca gacgtggagg gccactgagc          50
cccgctaccc gccccacagc ctttcctacc cagtgcagat cgcccggacg         100
cacacggacg tcgggctcct ggagtaccag caccactccc gcgactatgc         150
ctcccacctg tcgccgggct ccatcatcca gccccagcgg cggaggccct         200
ccctgctgtc tgagttccag cccgggaatg aacggtccca ggagctccac         250
ctgcggccag agtcccactc atacctgccc gagctgggga agtcagagat         300
ggagttcatt gaaagcaagc gccctcggct agagctgctg cctgaccccc         350
tgctgcgacc gtcacccctg ctggccacgg gccagcctgc gggatctgaa         400
gacctcacca aggaccgtag cctgacgggc aagctggaac cggtgtctcc         450
ccccagcccc ccgcacactg accctgagct ggagctggtg ccgccacggc         500
tgtccaagga ggagctgatc cagaacatgg accgcgtgga ccgagagatc         550
accatggtag agcagcagat ctctaagctg aagaagaagc agcaacagct         600
ggaggaggag gctgccaagc cgcccgagcc tgagaagccc gtgtcaccgc         650
cgcccatcga gtcgaagcac cgcagcctgg tgcagatcat ctacgacgag         700
aaccggaaga aggctgaagc tgcacatcgg attctggaag gcctggggcc         750
ccaggtggag ctgccgctgt acaaccagcc ctccgacacc cggcagtatc         800
atgagaacat caaaataaac caggcgatgc ggaagaagct aatcttgtac         850
ttcaagagga ggaatcacgc tcggaaacaa tggaagcaga agttctgcca         900
gcgctatgac cagctcatgg aggccttgga aaaaaggtg gagcgcatcg         950 aaaacaaccc gcgccggcgg gccaaggaga gcaaggtgcg cgagtactac        1000
gaaaagcagt tccctgagat ccgcaagcag cgcgagctgc aggagcgcat        1050
gcagagcagg gtgggccagc ggggcagtgg gctgtccatg tcggccgccc        1100
gcagcgagca cgaggtgtca gagatcatcg atggcctctc agagcaggag        1150
aacctggaga agcagatgcg ccagctggcc gtgatcccgc ccatgctgta        1200
cgacgctgac cagcagcgca tcaagttcat caacatgaac gggcttatgg        1250
```

-continued

| | |
|---|---|
| ccgaccccat gaaggtgtac aaagaccgcc aggtcatgaa catgtggagt | 1300 |
| gagcaggaga aggagacctt ccgggagaag ttcatgcagc atcccaagaa | 1350 |
| ctttggcctg atcgcatcat tcctggagag gaagacagtg gctgagtgcg | 1400 |
| tcctctatta ctacctgact aagaagaatg agaactataa gagcctggtg | 1450 |
| agacggagct atcggcgccg cggcaagagc cagcagcaac aacagcagca | 1500 |
| gcagcagcag cagcagcagc agcagcagca gcccatgccc cgcagcagcc | 1550 |
| aggaggagaa agatgagaag gagaaggaaa aggaggcgga aaggaggag | 1600 |
| gagaagccgg aggtggagaa cgacaaggaa gacctcctca aggagaagac | 1650 |
| agacgacacc tcaggggagg acaacgacga gaaggaggct gtggcctcca | 1700 |
| aaggccgcaa aactgccaac agccaggaa gacgcaaagg ccgcatcacc | 1750 |
| cgctcaatgg ctaatgaggc caacagcgag gaggccatca ccccccagca | 1800 |
| gagcgccgag ctggcctcca tggagctgaa tgagagttct cgctggacag | 1850 |
| aagaagaaat ggaaacagcc aagaaaggtc tcctggaaca cggccgcaac | 1900 |
| tggtcggcca tcgcccggat ggtgggctcc aagactgtgt cgcagtgtaa | 1950 |
| gaacttctac ttcaactaca agaagaggca gaacctcgat gagatcttgc | 2000 |
| agcagcacaa gctgaagatg gagaaggaga ggaacgcgcg gaggaagaag | 2050 |
| aagaaagcgc cggcggcggc cagcgaggag gctgcattcc cgcccgtggt | 2100 |
| ggaggatgag gagatggagg cgtcgggcgt gagcggaaat gaggaggaga | 2150 |
| tggtggagga ggctgaagcc ttacatgcct ctgggaatga ggtgcccaga | 2200 |
| ggggaatgca gtggcccagc cactgtcaac aacagctcag acaccgagag | 2250 |
| catcccctct cctcacactg aggccgccaa ggacacaggg cagaatgggc | 2300 |
| ccaagccccc agccaccctg ggcgccgacg ggccacccc aggcccaccc | 2350 |
| accccaccac ggaggacatc ccgggccccc attgagccca cccggcctc | 2400 |
| tgaagccacc ggagccccta cgcccccacc agcacccca tcgccctctg | 2450 |
| cacctcctcc tgtggtcccc aaggaggaga aggaggagga gaccgcagca | 2500 |
| gcgcccccag tggaggaggg ggaggagcag aagcccccg cggctgagga | 2550 |
| gctggcagtg gacacaggga aggccgagga gcccgtcaag agcgagtgca | 2600 |
| cggaggaagc cgaggagggg ccggccaagg gcaaggacgc ggaggccgct | 2650 |
| gaggccacgg ccgaggggc gctcaaggca gagaagaagg agggcgggag | 2700 |
| cggcagggcc accactgcca agagctcggg cgcccccag gacagcgact | 2750 |
| ccagtgctac ctgcagtgca gacgaggtgg atgaggccga gggcggcgac | 2800 |
| aagaaccggc tgctgtcccc aaggcccagc ctcctcaccc cgactggcga | 2850 |
| cccccgggcc aatgcctcac cccagaagcc actggacctg aagcagctga | 2900 |
| agcagcgagc ggctgccatc cccccatcc aggtcaccaa agtccatgag | 2950 |
| cccccccggg aggacgcagc tcccaccaag ccagctcccc cagccccacc | 3000 |
| gccaccgcaa aacctgcagc cggagagcga cgcccctcag cagcctggca | 3050 |
| gcagcccccg gggcaagagc aggagcccgg cacccccgc cgacaaggag | 3100 |
| gccttcgcag ccgaggccca gaagctgcct ggggacccc cttgctggac | 3150 |
| ttccggcctg cccttcccg tgccccccg tgaggtgatc aaggcctccc | 3200 |
| cgcatgcccc ggacccctca gccttctcct acgctccacc tggtcaccca | 3250 |

-continued

| | |
|---|---|
| ctgcccctgg gcctccatga cactgcccgg cccgtcctgc cgcgcccacc | 3300 |
| caccatctcc aacccgcctc ccctcatctc ctctgccaag caccccagcg | 3350 |
| tcctcgagag gcaaataggt gccatctccc aaggaatgtc ggtccagctc | 3400 |
| cacgtcccgt actcagagca tgccaaggcc ccggtgggcc ctgtcaccat | 3450 |
| ggggctgccc ctgcccatgg accccaaaaa gctggcaccc ttcagcggag | 3500 |
| tgaagcagga gcagctgtcc ccacggggcc aggctgggcc accggagagc | 3550 |
| ctggggggtgc ccacagccca ggaggcgtcc gtgctgagag ggacagctct | 3600 |
| gggctcagtt ccgggcggaa gcatcaccaa aggcattccc agcacacggg | 3650 |
| tgccctcgga cagcgccatc acataccgcg gctccatcac ccacggcacg | 3700 |
| ccagctgacg tcctgtacaa gggcaccatc accaggatca tcggcgagga | 3750 |
| cagcccgagt cgcttggacc gcggccggga ggacagcctg cccaagggcc | 3800 |
| acgtcatcta cgaaggcaag aagggccacg tcttgtccta tgagggtggc | 3850 |
| atgtctgtga cccagtgctc caaggaggac ggcagaagca gctcaggacc | 3900 |
| cccccatgag acggccgccc ccaagcgcac ctatgacatg atggagggcc | 3950 |
| gcgtgggcag agccatctcc tcagccagca tcgaaggtct catgggccgt | 4000 |
| gccatcccgc cggagcgaca cagcccccac cacctcaaag agcagcacca | 4050 |
| catccgcggg tccatcacac aagggatccc tcggtcctac gtggaggcac | 4100 |
| aggaggacta cctgcgtcgg gaggccaagc tcctaaagcg ggagggcacg | 4150 |
| cctccgcccc caccgccctc acgggacctg accgaggcct acaagacgca | 4200 |
| ggccctgggc cccctgaagc tgaagccggc ccatggggc ctggtggcca | 4250 |
| cggtgaagga ggcgggccgc tccatccatg agatcccgcg cgaggagctg | 4300 |
| cggcacacgc ccgagctgcc cctggccccg cggccgctca aggagggctc | 4350 |
| catcacgcag ggcaccccgc tcaagtacga caccggcgcg tccaccactg | 4400 |
| gctccaaaaa gcacgacgta cgctcccctca tcggcagccc cggccggacg | 4450 |
| ttcccacccg tgcacccgct ggatgtgatg gccgacgccc gggcactgga | 4500 |
| acgtgcctgc tacgaggaga gcctgaagag ccggccaggg accgccagca | 4550 |
| gctcgggggg ctccattgcg cgcggcgccc cggtcattgt gcctgagctg | 4600 |
| ggtaagccgc ggcagagccc cctgacctat gaggaccacg gggcacccctt | 4650 |
| tgccggccac ctcccacgag gttcgcccgt gaccatgcgg gagcccacgc | 4700 |
| cgcgcctgca ggagggcagc ctttcgtcca gcaaggcatc ccaggaccga | 4750 |
| aagctgacgt cgacgcctcg tgagatcgcc aagtccccgc acagcaccgt | 4800 |
| gcccgagcac cacccacacc ccatctcgcc ctatgagcac ctgcttcggg | 4850 |
| gcgtgagtgg cgtggacctg tatcgcagcc acatcccccct ggccttcgac | 4900 |
| cccacctcca taccccgcgg catccctctg gacgcagccg ctgcctacta | 4950 |
| cctgccccga cacctggccc ccaaccccac ctacccgcac ctgtacccac | 5000 |
| cctacctcat ccgcggctac cccgacacgg cggcgctgga gaaccggcag | 5050 |
| accatcatca atgactacat cacctcgcag cagatgcacc acaacacggc | 5100 |
| caccgccatg gcccagcgag ctgatatgct gaggggcctc tcgccccgcg | 5150 |
| agtcctcgct ggcactcaac tacgctgcgg gtccccgagg catcatcgac | 5200 |

```
ctgtcccaag tgccacacct gcctgtgctc gtgccccga caccaggcac      5250
cccagccacc gccatggacc gccttgccta cctccccacc gcgccccagc      5300
ccttcagcag ccgccacagc agctcccac tctccccagg aggtccaaca       5350
cacttgacaa aaccaaccac cacgtcctcg tccgagcggg agcgagaccg      5400
ggatcgagag cgggaccggg atcgggagcg ggaaaagtcc atcctcacgt      5450
ccaccacgac ggtggagcac gcacccatct ggagacctgg tacagagcag     5500
agcagcggca gcagcggcag cagcggcggg ggtgggggca gcagcagccg     5550
ccccgcctcc cactcccatg cccaccagca ctcgcccatc tcccctcgga     5600
cccaggatgc cctccagcag agacccagtg tgcttcacaa cacaggcatg     5650
aagggtatca tcaccgctgt ggagcccagc aagcccacgg tcctgaggtc      5700
cacctccacc tcctcacccg ttcgcccagc tgccacattc ccacctgcca      5750
cccactgcca actgggcggc accctcgatg gggtctaccc taccctcatg      5800
gagcccgtct tgctgcccaa ggaggccccc cgggtcgccc ggccagagcg     5850
gccccgagca gacaccggcc atgccttcct cgccaagccc ccagcccgct     5900
ccgggctgga gcccgcctcc tccccagca agggctcgga gccccggccc      5950
ctagtgcctc ctgtctctgg ccacgccacc atcgcccgca ccctgcgaa      6000
gaacctcgca cctcaccacg ccagcccgga cccgccggcg ccacctgcct     6050
cggcctcgga cccgcaccgg gaaaagactc aaagtaaacc cttttccatc      6100
caggaactgg aactccgttc tctgggttac cacggcagca gctacagccc      6150
cgaaggggtg gagcccgtca gccctgtgag ctcacccagt ctgacccacg     6200
acaagggggct ccccaagcac ctggaagagc tcgacaagag ccacctggag    6250
ggggagctgc ggcccaagca gccaggcccc gtgaagcttg gcggggaggc    6300
cgcccacctc ccacacctgc ggccgctgcc tgagagccag ccctcgtcca     6350
gcccgctgct ccagaccgcc caggggtca aaggtcacca gcgggtggtc      6400
accctggccc agcacatcag tgaggtcatc acacaggact acacccggca     6450
ccacccacag cagctcagcg cacccctgcc cgcccccctc tactccttcc     6500
ctggggccag ctgccccgtc ctggacctcc gccgcccacc cagtgacctc     6550
tacctcccgc ccccggacca tggtgccccg gcccgtggct cccccacag     6600
cgaaggggggc aagaggtctc cagagccaaa caagacgtcg gtcttgggtg    6650
gtggtgagga cggtattgaa cctgtgtccc caccggaggg catgacggag     6700
ccagggcact cccggagtgc tgtgtacccg ctgctgtacc gggatgggga     6750
acagacggag cccagcagga tgggctccaa gtctccaggc aacaccagcc     6800
agccgccagc cttcttcagc aagctgaccg agagcaactc cgccatggtc      6850
aagtccaaga agcaagagat caacaagaag ctgaacaccc acaaccggaa    6900
tgagcctgaa tacaatatca gccagcctgg gacggagatc ttcaatatgc      6950
ccgccatcac cggaacaggc cttatgacct atagaagcca ggcggtgcag    7000
gaacatgcca gcaccaacat ggggctggag gccataatta gaaaggcact    7050
catgggtaaa tatgaccagt gggaagagtc cccgccgctc agcgccaatg    7100
cttttaaccc tctgaatgcc agtgccagcc tgccgctgc tatgcccata      7150
accgctgctg acggacggag tgaccacaca ctcacctcgc caggtggcgg    7200
```

-continued

```
cgggaaggcc aaggtctctg gcagacccag cagccgaaaa gccaagtccc      7250
cggccccggg cctggcatct ggggaccggc caccctctgt ctcctcagtg      7300
cactcggagg gagactgcaa ccgccggacg ccgctcacca accgcgtgtg      7350
ggaggacagg ccctcgtccg caggttccac gccattcccc tacaaccccc      7400
tgatcatgcg gctgcaggcg ggtgtcatgg cttccccacc cccaccgggc      7450
ctccccgcgg gcagcgggcc cctcgctggc ccccaccacg cctgggacga      7500
ggagcccaag ccactgctct gctcgcagta cgagacactc tccgacagcg      7550
agtgactcag aacagggcgg gggggggcgg gcggtgtcag gtcccagcga      7600
gccacaggaa cggccctgca ggagcggggc ggctgccgac tcccccaacc      7650
aaggaaggag ccectgagtc cgcctgcgcc tccatccatc tgtccgtcca      7700
gagccggcat ccttgcctgt ctaaagcctt aactaagact cccgcccgg      7750 gctggccctg tgcagaccTt actcagggga tgtttacctg gtgctcggga      7800 agggaggggga aggggccggg gaggggggcac ggcaggcgtg tggcagccac     7850
acacaggcgg ccagggcggc cagggaccca aagcaggatg accacgcacc      7900
tccacgccac tgcctcccc gaatgcattt ggaaccaaag tctaaactga       7950
gctcgcagcc cccgcgccct ccctccgcct cccatcccgc ttagcgctct      8000
ggacagatgg acgcaggccc tgtccagccc ccagtgcgct cgttccggtc      8050
cccacagact gccccagcca acgagattgc tggaaaccaa gtcaggccag      8100
gtgggcggac aaaagggcca ggtgcggcct gggggggaacg gatgctccga     8150 ggactggact gttttttca cacatcgttg ccgcagcggt gggaaggaaa       8200
ggcagatgta aatgatgtgt tggtttacag ggtatatttt tgataccttc      8250
aatgaattaa ttcagatgtt ttacgcaagg aaggacttac ccagtattac      8300
tgctgctgtg cttttgatct ctgcttaccg ttcaagaggc gtgtgcaggc      8350
cgacagtcgg tgaccccatc actcgcagga ccaagggggc ggggactgct      8400
cgtcacgccc cgctgtgtcc tccctccctc ccttccttgg gcagaatgaa      8450
ttcgatgcgt attctgtggc cgccatttgc gcagggtggt ggtattctgt      8500
catttacaca cgtcgttcta attaaaaagc gaattatact ccaaaaaaaa      8550
aaaaaaaaaa a                                                 8561
```